(12) United States Patent
Gammon

(10) Patent No.: US 6,823,741 B2
(45) Date of Patent: Nov. 30, 2004

(54) WEAR GAUGE

(75) Inventor: Howard M. Gammon, Sea Girt, NJ (US)

(73) Assignee: Gammon Technical Products, Inc., Manasquan, NJ (US)

(*) Notice: Subject to any disclaimer, the term of this patent is extended or adjusted under 35 U.S.C. 154(b) by 0 days.

(21) Appl. No.: 10/448,637

(22) Filed: May 30, 2003

(65) Prior Publication Data
US 2003/0230134 A1 Dec. 18, 2003

Related U.S. Application Data
(60) Provisional application No. 60/389,370, filed on Jun. 17, 2002.

(51) Int. Cl.⁷ ............................................. G01N 19/08
(52) U.S. Cl. ....................................................... 73/799
(58) Field of Search .......................... 73/774, 799, 804, 73/856

(56) References Cited

U.S. PATENT DOCUMENTS

| | | | | |
|---|---|---|---|---|
| 4,093,883 A | * | 6/1978 | Yamamoto | 310/317 |
| 5,109,609 A | | 5/1992 | Anderson | |
| 5,513,726 A | * | 5/1996 | Thompson et al. | 188/1.11 L |
| 5,535,854 A | * | 7/1996 | Prince | 188/1.11 R |
| 5,562,045 A | * | 10/1996 | Rudibaugh et al. | 105/224.1 |
| 5,926,001 A | * | 7/1999 | Eguchi | 318/647 |

FOREIGN PATENT DOCUMENTS

| | | | | |
|---|---|---|---|---|
| GB | 2390428 A | * | 1/2004 | G01B/3/30 |
| JP | 8136205 A | | 5/1996 | |

* cited by examiner

Primary Examiner—Max Noori
(74) Attorney, Agent, or Firm—Fraser Martin Buchanan Miller LLC; Donald R. Fraser

(57) ABSTRACT

A wear gauge for determining excessive wear of the notches and lugs of an aircraft fueling nozzle adapter to expeditiously sense wear which might result in leakage of fuel during an aircraft refueling operation.

4 Claims, 2 Drawing Sheets

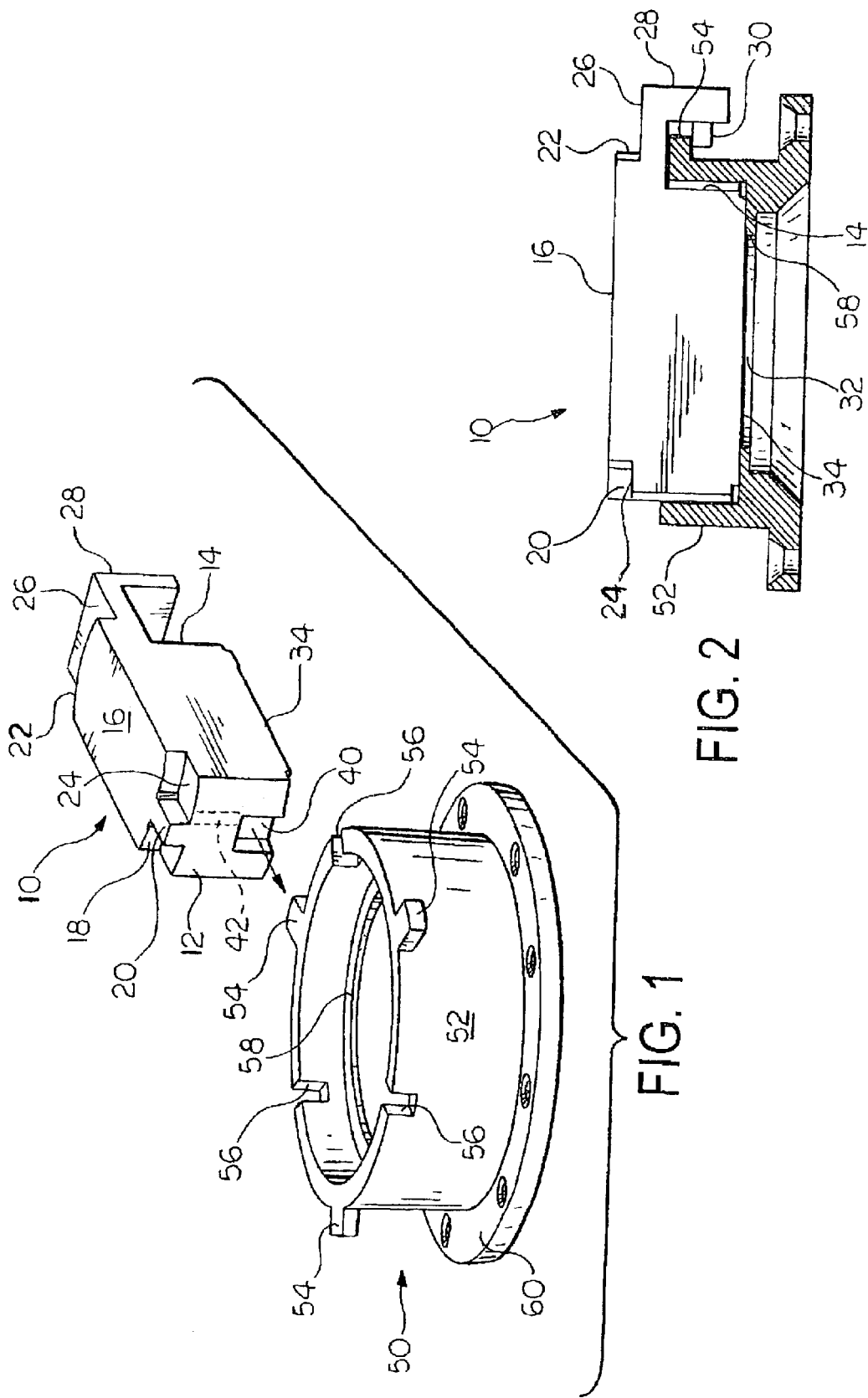

WEAR GAUGE

This is a continuation of provisional patent application Ser. No. 60/389,370, filed Jun. 17, 2002.

BACKGROUND OF THE INVENTION

1. Field of the Invention

The present invention relates to wear gauges and more particularly to a gauging device used to check for excessive wear on aircraft fueling adapters.

2. Description of the Prior Art

The design of an aircraft fueling adapter is controlled worldwide on all jet fuel powered aircraft that are equipped for pressure fueling except for some U.S. Army helicopters. The problem of excessive wear on aircraft fueling adapters has caused many problems for many years.

These adapters are used not only on aircraft, but also on refueler trucks, so that the trucks can be filled from ground-based apparatus. The adapters are designed to be connected to the refueling nozzle. The nozzle can be opened to permit the flow of fuel only when the nozzle is in a fully latched position. By opening the nozzle, a valve in the adapter is caused to be opened by allowing fuel to flow into the aircraft. As long as the nozzle valve remains open, it is impossible to remove the nozzle by means of a mechanical interlock system. However, in the event there is excessive wear on certain portions of the adapter, the nozzle can actually be removed causing a spill.

It is an object of the present invention to produce a wear gauge to monitor the wear of fueling nozzle adapters and prevent unwanted spills and the like.

SUMMARY OF THE INVENTION

The above object, as well as others, may surprisingly be achieved by a wear gauge for checking excessive wear of the notches and lugs on fueling nozzle adapters comprising an elongate body having a first end wall, a spaced apart second end wall, a top wall, and a bottom wall; the top wall including an upstanding shoulder contoured to be received by the adapter and an outwardly extending finger; the bottom wall including spaced apart parallel rails for contact with the sealing surface of the adapter provided to contact the fuel nozzle nose seal and terminate short of the juncture of the bottom wall and the associated first and second end walls to form a shoulder for receiving the peripheral portion of the adapter sealing surface; the first end wall including a notch sized to normally prevent the entrance therein of any of the radially outwardly extending adapter lugs; and the second end wall including a downwardly extending leg spaced from the body and having an inwardly extending dowel pin and normally preventing passage of the outwardly extending adapter lugs.

BRIEF DESCRIPTION OF THE DRAWINGS

The above object and advantages of the invention will become readily apparent to one skilled in the art from reading the following detailed description of the invention when considered in the light of the accompanying drawings, in which FIG. 1 is an exploded view of a wear gauge incorporating the features of the invention preparatory to measuring wear on an associated typical aircraft fueling nozzle adapter;

FIG. 2 is a cross sectional view of the wear gauge illustrated in FIG. 1 in operative position to measure for possible excessive wear of the surfaces of the radially outwardly extending lugs of the adapter;

DETAILED DESCRIPTION OF THE PREFERRED EMBODIMENT OF THE INVENTION

Figure 3:
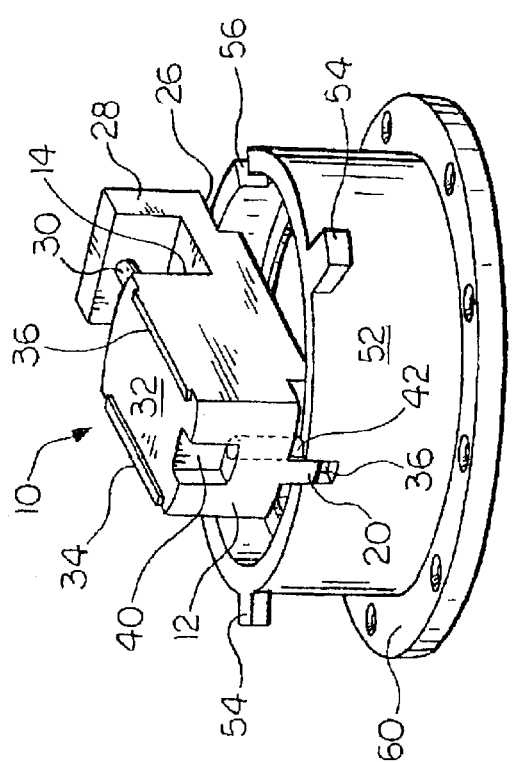
FIG. 3 is a perspective view of the wear gauge in operative position to measure for excessive wear of the upwardly opening notches of the adapter.

Referring to the drawings, there is illustrated the preferred embodiment of the invention. The following description is divided into sections dealing with each of the wear measurements of an aircraft fueling nozzle adapter wherein the measurements were deemed critical in respect of the operation of the fueling system.

The wear gauge embodying the novel features of the invention is designated by reference numeral 10 and the associated fueling nozzle adapter to be measured is designated by reference numeral 50. The wear gauge 10 includes a main elongate body portion having a first end wall 12 which is arcuately formed on the same or substantially the same radius as the inner surface of the cylindrical wall 52 of the nozzle adapter 50. The main body portion also includes a second end wall 14 spaced apart from and having the same curvature as the spaced apart end wall 12. A top wall 16 is provided which is caused to terminate in depending spaced apart curved shoulders 18 and 22 which are formed on the same radius as the end walls 12 and 14. A finger 20 extends outwardly from the shoulder 18 and terminates at the first end wall 12. A supporting surface 24 extends from the shoulder 18 on opposite sides of the finger 20 and terminates at the end wall 12. An associated spaced apart supporting surface 26 extends from the shoulder 22 and terminates in a depending end wall 28 which is spaced from the end wall 14. As illustrated in FIGS. 2, 3, 4 and 5, a pin 30 is caused to extend from the depending end wall 28. The pin 30 extends a sufficient distance into the gap between the walls 14 and 28 to contact the undersurface of the radially outwardly extending lugs 54 of the fueling nozzle adapter 50 as clearly illustrated in FIG. 2.

A bottom wall 32, clearly illustrated in FIGS. 2 and 3, opposite the top wall 16 is provided which extends between the first end wall 12 and the second end wall 14. A pair of spaced apart parallel runners 34 and 36 depend from opposite sides of the bottom wall 32. The runners 34 and 36 extend less than the full length of the bottom wall and are dimensioned to be received within the zone defined by an annular rim 58 within the interior of the nozzle adapter 50.

A notch 40 is formed in the first end wall 12 spaced from the finger 20. The notch 40 is employed to test the wear of the width of the lugs 54 of the adapter 50, as will be explained hereinafter. A bore hole is formed in the wear gauge to extend from the notch 40 to the juncture of one side of the finger 20 and the adjacent supporting surface 24.

The fueling nozzle adapter 50 is typically formed of an aluminum alloy which tends to wear at surfaces thereof which contact with the associated fueling nozzles. Excessive wear has been found to cause fuel leakage during refueling operations. The adapter 50 includes a cylindrical wall 52 having a plurality of lugs 54 which extend radially outwardly from the periphery of an end of the cylindrical wall 52.

Interdigitated between the lugs 54 is an array of equidistantly displaced slots 56 which extend longitudinally from the end of the cylindrical wall 52.

The annular inwardly extending rim 58 is provided within the interior of the cylindrical wall 52 and functions as a sealing surface between the refueling nozzle and the adapter.

An annular flange 60 is formed at the end of the cylindrical wall 52 opposite the lugs 54 and the slots 56. The flange 60 is provided with a series of apertures for receiving fasteners for attachment of the adapter 50 to an associated aircraft or refueler truck, for example.

In operation, when the undersurface of one of the lugs 54 wears, it increases the sealing surface depth. However, wear of the sealing surface of the annular rim 58 also increases the sealing surface depth. The sealing surface depth determines the compression force on the nozzle nose seal and the adapter 50. Therefore, thickness measurement of the lugs 54 should be dropped from the consideration because the measurement of sealing surface depth in reference to the underside of the lugs serves this purpose.

The width of the slots 56 controls the primary safety interlock system of the adapter/nozzle assembly. There are three (3) locator pins in the nozzle that fit in the three (3) slots 56 of the adapter 50. If there is excessive slot wear, the nozzle may, under certain conditions, be removed from the adapter 50 before the poppet valves of the nozzle and adapter 50 have been closed, resulting in a fuel spill. Industry consensus determined that wear greater than 0.060" creates a potentially hazardous condition.

Wear occurs from two different actions:

1. Attachment of the nozzle to the adapter 50 results in impact by the locator pins against the clockwise sides of the slots 56.

2. Detachment of the nozzle results in impact by the pins against the counterclockwise sides of the slots 56.

Wear on the clockwise sides of the slots 56 is of no interest, because it has no influence on the safety interlock system. However, wear on the counterclockwise sides of the slots 56 definitely is important, because excessive wear can allow the nozzle to be removed or the seal contact force reduced enough to cause a fuel spill.

The wear on the counterclockwise sides should be limited to 0.060" at a depth of 0.10" from the adapter top face. At first consideration, it appears that this is difficult to measure, but it has been determined that it can be done easily because the pins of the nozzle are not long enough to reach the bottom of the slot. Therefore, the unworn side of a slot 56 becomes the datum for measurement of wear.

There are three measurements deemed necessary, as more specifically illustrated in the drawings.

The end face 12 of the gauge 10 has a slot 40 that is 0.425" wide. If any one of the three (3) adapter lugs 54 is able to enter the gauge slot 40, the adapter 50 fails, as illustrated in FIG. 1.

The gauge 10 must be inserted in the cavity of the adapter 50 as illustrated in FIG. 2 so that the two runners 34 and 36 rest on the worn surface of the sealing rim 58 where the nozzle nose seal makes contact. When rotating the gauge 10 clockwise, the dowel pin 30 approaches the underside of a lug 54. If the pin 30 passes under any one of the lugs 54, the lug 54 and/or seal surface 58 are excessively worn.

Figure 4:
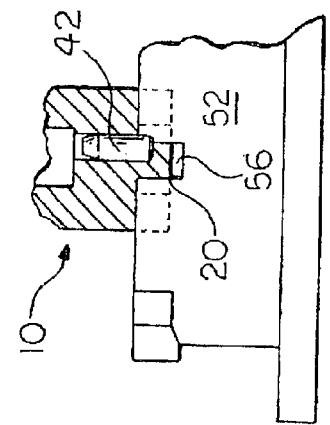
FIG. 4 is a fragmentary view partially in section showing the apparatus illustrated in FIG. 3 measuring a slot with acceptable wear.
Figure 5:
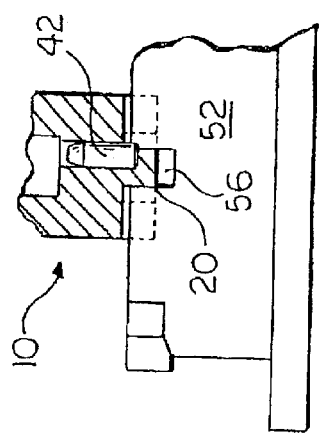
FIG. 5 is similar to FIG. 4 showing a slot with unacceptable wear.

The gauge 10 is inverted from the position shown in FIG. 2 so that the finger 20 having the small dowel pin 42 enters an adapter slot 56, as illustrated in FIGS. 3, 4, and 5. The opposite end of the gauge 10 must rest on the top face of the adapter 50, as shown. If the finger 20 enters any one of the three (3) slots 56 so that there is no gap between the gauge 10 and the top face of the adapter 50, the adapter 50 must be replaced.

In accordance with the provisions of the patent statutes, the present invention has been described in what is considered to represent its preferred embodiment. However, it should be understood that the invention can be practiced otherwise than as specifically illustrated and described without departing from its spirit or scope.

What is claimed is:

1. A wear gauge for checking excessive wear of the notches and lugs on a fueling nozzle adapter having a sealing surface comprising:

an elongate body having a first end wall, a spaced apart second end wall, a top wall, and a bottom wall;

said top wall including an upstanding shoulder contoured to be received by the adapter and an outwardly extending finger;

said bottom wall including spaced apart parallel rails for contact with the sealing surface of the adapter provided to contact the fueling nozzle nose seal;

said first end wall including a notch sized to normally prevent the entrance therein of any of the radially outwardly extending adapter lugs;

and said second end wall including a downwardly extending leg spaced from the body containing an inwardly extending dowel pin normally preventing passage of the outwardly extending adapter lugs between the pin and the leg.

2. A wear gauge as defined in claim 1 including a pin extending adjacent the finger of said top wall to prevent the finger and pin from entering the notches of the adapter.

3. A wear gauge as defined in claim 1 wherein the parallel rails of said bottom wall terminate short of the juncture of said bottom wall and said first and second spaced apart end walls to form a shoulder for receiving the sealing surface of the adapter.

4. A wear gauge as defined in claim 3 wherein the juncture of said bottom wall and said first and second spaced apart end walls is annular.

* * * * *